United States Patent
Ho et al.

(10) Patent No.: US 8,005,921 B2
(45) Date of Patent: Aug. 23, 2011

(54) REDUNDANT IMAGE STORAGE SYSTEM AND METHOD FOR PACS USING ARCHIVED FLAGS

(75) Inventors: Kinson Kin Sang Ho, Waterloo (CA); Peter Brian George Mayo, Baden (CA)

(73) Assignee: AGFA Inc., Toronto (CA)

( * ) Notice: Subject to any disclaimer, the term of this patent is extended or adjusted under 35 U.S.C. 154(b) by 637 days.

(21) Appl. No.: 11/593,593

(22) Filed: Nov. 7, 2006

(65) Prior Publication Data
US 2007/0107033 A1 May 10, 2007

Related U.S. Application Data

(60) Provisional application No. 60/733,797, filed on Nov. 7, 2005.

(51) Int. Cl.
*G06F 13/00* (2006.01)
(52) U.S. Cl. ....... 709/217; 711/162; 711/161; 714/4.11; 707/655; 707/610
(58) Field of Classification Search .................. 382/128; 705/2, 3; 707/204, 655, 610; 714/6, 15, 714/20, 4.11; 711/162, 161; 709/208, 217; 725/115.145
See application file for complete search history.

(56) References Cited

U.S. PATENT DOCUMENTS

| | | | |
|---|---|---|---|
| 5,671,350 A | 9/1997 | Wood | |
| 6,460,123 B1 | 10/2002 | Blumenau | |
| 6,502,105 B1 | 12/2002 | Yan et al. | |
| 6,529,757 B1 | 3/2003 | Patel et al. | |
| 6,564,225 B1 | 5/2003 | Brogliatti et al. | |
| 6,574,629 B1 * | 6/2003 | Cooke, Jr. et al. | 1/1 |
| 6,629,110 B2 | 9/2003 | Cane et al. | |
| 6,799,206 B1 | 9/2004 | Workman et al. | |
| 7,058,853 B1 * | 6/2006 | Kavanappillil et al. | 714/13 |
| 7,844,571 B2 * | 11/2010 | Konig | 707/602 |
| 2002/0052884 A1 * | 5/2002 | Farber et al. | 707/104.1 |
| 2002/0056634 A1 * | 5/2002 | Pitts et al. | 204/164 |
| 2002/0087588 A1 | 7/2002 | McBride | |
| 2002/0152231 A1 | 10/2002 | Silva-Craig et al. | |
| 2004/0015373 A1 * | 1/2004 | Silva-Craig et al. | 705/3 |

(Continued)

FOREIGN PATENT DOCUMENTS

JP 2003316626 A * 11/2003

OTHER PUBLICATIONS

English Translation of JP2003-316626A, Nov. 7, 2003, Yamade K, pp. 1-16.*

(Continued)

*Primary Examiner* — Hong Kim
(74) *Attorney, Agent, or Firm* — Bereskin & Parr LLP; Isis E. Caulder

(57) ABSTRACT

A redundant image storage system for archiving an image data file within at least two picture archiving and communication systems (PACS), said system including coupled source and destination PACS networks. The source PACS network stores and transmits the image data file. The destination PACS is associated with a Remote Archive Locations record and a Source PACS Archived flag. The destination PACS network receives the image data file from the source PACS network, stores the image data file and determines whether the image data file should be stored back on the source PACS network and if not then sets the value of the Source PACS Archived flag to be true. The destination PACS network only sends the image data file to the source PACS network for storage if the Source PACS Archived flag is false.

19 Claims, 11 Drawing Sheets

U.S. PATENT DOCUMENTS

2005/0235122 A1* 10/2005 Pillai et al. .................... 711/162
2006/0005048 A1* 1/2006 Osaki et al. .................... 713/193

OTHER PUBLICATIONS

European Search Report dated Oct. 10, 2007.
European Examination Report, 2007.

Digital Imaging and Communications in Medicine (DICOM) Part 1: Introduction and Overview, 2004, National Electrical Manufacturers Association, Rosslyn, Virginia, U.S.A.

Digital Imaging and Communications in Medicine (DICOM) Part 4: Service Class Specifications, 2004, National Electrical Manufacturers Association, Rosslyn, Virginia, U.S.A.

* cited by examiner

REDUNDANT IMAGE STORAGE SYSTEM AND METHOD FOR PACS USING ARCHIVED FLAGS

This application claims the benefit under 35 U.S.C. 119(e) of U.S. Provisional Patent Application No. 60/733,797, filed Nov. 7, 2005, the contents of which are incorporated by reference herein.

FIELD

This invention relates generally to the field of image storage and particularly to an improved redundant image storage system and method.

BACKGROUND

Medical imaging has been an expanding field for several decades. With increasing diagnostic tools, increasing population, more wide-spread access to medical treatment, and the desirability of sharing information between doctors and professionals, medical imaging is likely to continue growing. To address this continued growth, and the subsequent inconveniences of paper and other fixed forms of medical image storage, the medical community has increasingly turned to digital forms of image storage.

Picture Archiving and Communications Systems (PACS) are a popular example of a digital image system. These systems connect elements such as imaging modalities, storage databases or areas, clients that use the medical image data, and data processing devices to create a network of imaging technology. Such systems then provide easier remote diagnosis and data access, sharing of information between health-care professionals, and ultimately a better health-care system.

In what is termed a "Store and Remember" configuration, a first PACS network can utilize a second PACS network as a long-term storage solution. In this configuration the problem of long-term data storage is offloaded to the second PACS network. This can be useful for many situations and is an instance of buffering or caching as it is known in the industry. This also has the benefit of effectively publishing images to a broader audience that includes users with access to the second PACS network as well as the first. This can be done as either a substitute for other types of long-term storage or in addition to local archival.

In a mirroring configuration, multiple PACS networks can utilize each other as redundant storage locations to ensure that image data files are properly archived (i.e. "mirrored") to provide additional protection against loss and to allow image data files at one PACS network to be viewed at another PACS network. However, when two or more related PACS networks use each other as redundant storage locations, the resulting flow of image data files being archived can result in what is termed "looping" or cyclic storage activity.

As an illustration of this consider an image data file being sent by a source PACS network to a destination PACS network for archiving (i.e. redundant storage). If the destination PACS network is configured to store to the source PACS network (i.e. to automatically request archiving of any image data file it receives on the source PACS network) then the image data file will unnecessarily be queued up for archiving back to the source PACS network. If the source PACS network is configured to accept duplicates, then the source PACS network will receive the same image data file and again queue the image data file for archiving back to the destination PACS network. However, since the image data file originated from the source PACS network and accordingly is already known and archived at the source PACS network, the image data file does not require re-archiving at the source PACS network.

Such cyclic archiving results in a high and continuous volume of unnecessary image data transmissions between source and destination PACS networks. In addition, if it is not apparent to a destination PACS network whether an image data file has been archived and previously pre-processed and checked at the source PACS network then the destination PACS network may conduct additional unnecessary processing such as OCR, field mappings, HIS verification, and compression.

Most image archiving systems that have been designed for PACS networks either are single-location archives where image data files are not transmitted remotely or utilize a master-slave configuration. In these kinds of image archiving systems, there is only one direction of archiving (i.e. slaves are the only networks that send unsolicited images to their masters) and accordingly, the issue of cyclic archiving is not a concern. However, in situations where there is a master archive that is also a slave to one of it's own slaves (i.e. in PACS archive mirroring), cyclic archiving difficulties are problematic.

The negative impact of "looping" or cyclic archiving on network efficiency can be severely compounded when three or more PACS networks are involved. For example, where an image data file is sent by a first PACS network to a second PACS network for archiving, the second PACS network automatically sends the image data file to a third PACS network for archiving and then the third PACS automatically sends the image data file back to the first PACS network to be re-archived and so on. The negative effects associated with "looping" or cyclic archiving dramatically increase the cost of archiving image data files within a PACS network.

SUMMARY

The invention provides in one aspect, a redundant image storage system for archiving an image data file having an image data identifier within at least two picture archiving and communication system (PACS) networks, said system comprising:
 (a) a source PACS network including:
  (i) a source storage device for storing the image data file;
  (ii) a source processor coupled to the source storage device, the source processor being adapted to retrieve the image data file from the source storage device and transmitting the image data file to another PACS network;
 (b) a first destination PACS network coupled to the source PACS network, the first destination PACS network including:
  (iii) a Boolean source PACS Archived flag associated with the image data identifier and the source PACS network;
  (iv) a destination storage device for storing the image data file;
  (v) a destination processor coupled to the destination storage device, said destination processor being adapted to:
   (A) receive the image data file from the source PACS network and store the image data file in the destination storage device;
   (B) determine whether the image data file should also be stored back in the source PACS network;
   (C) if (B) is false, then setting the value of the source PACS Archived flag to true;
   (D) send the image data file to the source PACS network for storage only if the source PACS Archived flag is false.

The invention provides in another aspect, a method for archiving an image data file having an image data identifier within at least a source archiving and communication system (PACS) network and a destination archiving and communication system (PACS) network, said method comprising:

(a) storing the image data file in the source PACS network;
(b) retrieving the image data file from the source PACS network and transmitting the image data file to the first destination PACS network;
(c) associating a Boolean source PACS Archived flag with the image data identifier and the source PACS network;
(d) receiving the image data file from the source PACS network and storing the image data file in the first destination PACS network;
(e) determining whether the image data file should also be stored back in the source PACS network;
(f) if (e) is false, then setting the value of the source PACS Archived flag to true; and
(g) sending the image data file to the source PACS network for storage only if the source PACS Archived flag is false.

Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

Figure 1:
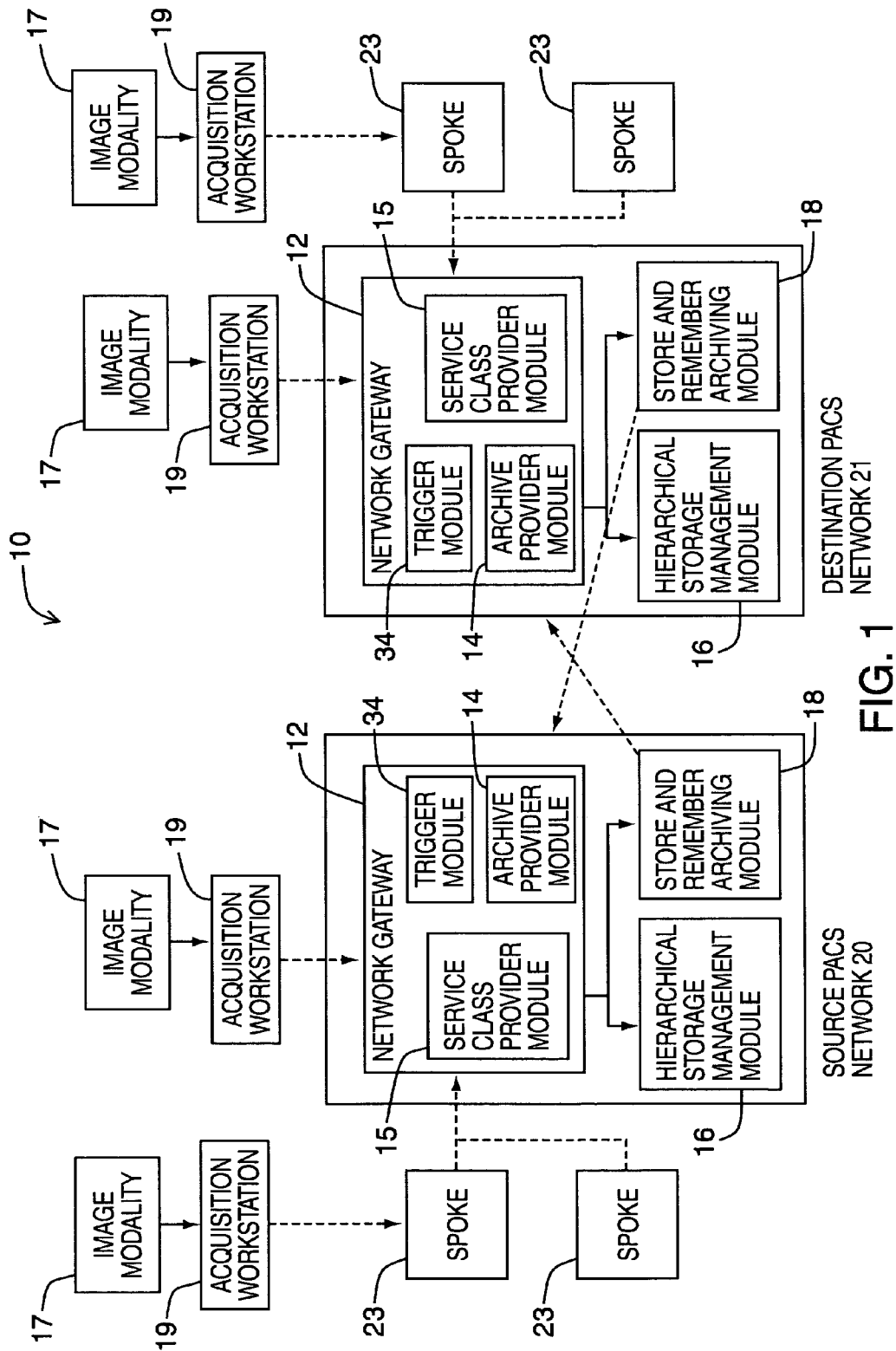
FIG. 1 is a block diagram of the components of an exemplary embodiment of a redundant image storage system.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), at least one input device, and at least one output device. For example and without limitation, the programmable computers may be a mainframe computer, server, personal computer, laptop, personal data assistant, or cellular telephone. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Reference is first made to FIG. 1, which illustrates the components of a redundant image storage system 10 made in accordance with an exemplary embodiment. The redundant image storage system 10 includes a plurality of imaging modalities 17 and acquisition workstations 19, a source Picture Archiving and Communications Systems (PACS) network 20 and a destination PACS network 21. Imaging modality 17 generates various types of medical image, non-image, displayable and non-displayable data which is then acquired by an acquisition workstation 19 and reformatted into an image data file that is then in turn stored in the source PACS network 20 as will be further discussed.

Source and destination PACS networks 20, 21 further comprise a network gateway 12 that includes a service class provider (SCP) module 15 and an archive provider module 14, a local archive module 16 such as a hierarchical storage management (HSM) module 16, and a store and remember (S&R) archiving module 18. Image archiving system 10 provides for improved archive mirroring as between source and destination PACS networks 20 and 21, which results in added protection against loss of data and allows image data files stored on destination PACS network 21 to be viewed at source PACS network 20 and vice versa.

In an exemplary embodiment, redundant image storage system 10 is implemented to comply with conventional DICOM digital image handling standards such that source and destination PACS networks 20 and 21 and spoke PACS networks 23 all operate within the DICOM environment. The DICOM environment supports C-STORE operations that are used within DICOM's Storage Service Class to facilitate transfer of image data files as will be further described. If a C-STORE operation cannot be completed successfully, the C-STORE response will contain a status code defining the reason for the failure, as well as whether the failure was transient or permanent.

In addition, as shown in FIG. 1, redundant image storage system 10 also embodies a hub and spoke model where each of the source and destination PACS networks 20 and 21 are considered to be hubs (i.e. suitable for use as an enterprise archive server). As hubs, the source and destination PACS networks 20 and 21 operate as a secondary archive, where each user can access each hub through a local spoke PACS network 23 (or image processing cluster). Functionally, the spoke clusters 23 represent the previously referenced common slave networks that have a basic master-slave relationship with the master PACS networks in the hub.

Finally, while redundant image storage system 10 is being described in terms of a source and destination PACS networks 20 and 21, it should be understood that that this convention is being adopted for illustrative purposes and that the described functional relationship between the source and destination PACS networks 20 and 21 could exist between any two PACS networks within a larger PACS network of more than two PACS networks. In addition, while the flow of the image data file is illustrated as flowing from the source PACS network 20 to the destination PACS network 21, it should be understood that the flow of the image data file could just as easily flow the other way in which case the destination PACS network 21 would be considered the "source" and the source PACS network 20 would be considered the "destination" for purposes of the exemplary embodiments discussed.

Furthermore the full complexity of the situation is realized when image data files are flowing in both directions (i.e. between source and destination PACS networks 20 and 21) simultaneously. That is, as image data files are transmitted between both PACS networks 20 and 21 (i.e. each with its own image lifecycle) each PACS network 20 and 21 functions simultaneously as a "source PACS network" and as a "destination PACS network".

Also, all completed image data files are forwarded from the local spokes 23 to one of the hubs (i.e. one of the PACS networks). This model allows each local spoke 23 to have access to image data files created and input from other spokes 23 by providing searching of the SCP module 15 of each hub. The configuration illustrated by the exemplary embodiment of redundant image storage system 10 in FIG. 1 includes multiple hubs (i.e. enterprise archives) that provide redundancy between each other and where each hub handles a plurality of spokes 23.

The imaging modality 17 provides image data to the acquisition workstation 19 in any analog or digital format used to represent medical data (e.g. bitmaps, JPEGs, GIFs, etc.). Specifically, as conventionally known, the imaging modality 17 generates various types of medical image, non-image, displayable and non-displayable data (e.g. x-ray images, CT scan images, MRI images, structured report data, gray scale presentation state data, Mammography For-Processing object data etc.)

The acquisition workstation 19 then converts the image data into a digital format (i.e. an image data file) suitable for storage in the source PACS network 20 or a local spoke PACS network 23. In the medical imaging industry, standard image data files carry meta-data and have unique identifiers that can be used to commonly identify two different files as containing the same logical image. These identifiers will be referred to in this disclosure as "image data identifiers". Image data identifiers are also used to request the image from storage providers.

The acquisition workstation 19 may be a personal computer (e.g. a PC) or server that is physically separate from the imaging modality 17, or the acquisition workstation 19 may be separably or inseparably connected to the imaging modality 17. When the acquisition workstation 19 provides an image data file associated with image data to the source PACS network 20, the network gateway 12 stores a copy of the image data file for local storage. Medical image meta-data such as patient identifiers, patient names, study descriptions and image descriptions are obtained from the image data provided by the imaging modality 17 and also stored in a locally accessible database. Image data identifiers are also associated with each image data file. The clients of the source PACS network 20 are then able to access image data files from the source network gateway 12.

Accordingly, it should be understood that the term "image data file" as used in the present disclosure includes without restriction image data and image meta-data including image data identifiers. Also, it should be understood that the term "image data file" covers various kinds of digital image entities (e.g. series, studies, images, etc.) without exclusion. Finally, it should be understood that the term "image data file" can also refer to various non-image based files such as structured report files, gray scale presentation state files and the like as well as various non-displayable files such as Mammography For-Processing objects and the like without restriction.

The HSM module 16 is used for archival storage and retrieval of medical image data files among other things. The network gateway 12 also extracts associated meta-data from the image data files (i.e. patent, study, series and image) and stores this information. Although the HSM module 16 stores medical image data files that include image data and associated image meta-data, it may also be used to store other information not related to the redundant image storage system 10 (e.g. patient lists, reports, etc.) Original image data files stored within HSM module 16 can be further archived or backed up using PACS archive mirroring functionality as will be described.

In case of a disaster (i.e. loss of HSM module 16 on source PACS network 20) image data files may need to recovered from the HSM module 16 on destination PACS network 21, and perhaps recompressed for storage in HSM module 16 within source PACS network 20 again. This recovery may happen on an as-needed basis if/when the image data are requested in the future, or an entire lost HSM module 16 can be rebuilt using information concerning what was stored in the failed HSM module 16.

It should be understood that while for illustrative purposes in the present description, the source and destination PACS networks 20 and 21 are said to utilize a HSM local archive module 16, any generic local archive module 16 could be used instead.

The S&R archiving module 18 provides archiving facility to each of the source and destination PACS networks 20 and 21. Each S&R archiving module 18 can be set up to automatically ensure that image data files are stored to one or more other PACS networks. It is also possible for the S&R archiving modules 18 of two or more PACS networks to be configured to automatically ensure that image data files are redundantly stored to each other.

For example, source PACS network 20 can be configured such that its S&R archiving module 18 is set up to send image data files to the archive provider module 14 at the destination PACS network 21 (i.e. to send image data files for archiving at destination PACS network 21) and vice versa. In this example, the S&R archiving module 18 associated with a source PACS network 20 will initiate storage of an image data file to the destination PACS network 21 by issuing a C-STORE request that is handled by the network gateway 12 at the destination PACS network 21.

The network gateway 12 manages communication between acquisition workstations 19, spokes 23, and HSM module 16 and S&R archiving module 18. Typically, the network gateway 12 receives a request for an image data file from a client, determines the location of the requested image data within the source and destination PACS networks 20 and 21 and provides the client access to the image data file. The network gateway 12 is also able to communicate with and instruct the other components of the associated PACS network such as the HSM archive module 16 and the S&R archive module 18.

More specifically, the network gateway 12 includes the service class provider (SCP) module 15 and may include the archive provider module 14.

The SCP module 15 is utilized to respond to a C-STORE request from the S&R module 18 of another PACS network and to receive the image data file. The SCP module 15 then is configured to perform a series of checks on the image data file including Hospital Information System (HIS) verification and also to perform compression of the image data file, to apply field mappings and optical character recognition (OCR) on image data files as they arrive. The SCP module 15 also registers the meta-data and the initial file location information in a centrally accessible database for the coordinating components of the source and destination PACS networks 20 and 21 to use in their computations and services. Finally, the SCP module 15 will queue the image data file for archiving at all configured archives (e.g. other PACS networks that are setup for archive mirroring, or local archives).

The archive provider module 14 within the destination PACS network 21 is not used in the present exemplary embodiment, but will be referred to in respect of additional exemplary embodiments later in the disclosure.

While the components of the source and destination PACS networks 20 and 21 are depicted as separate elements, it should be understood by those skilled in the art that the network gateway 12, archive provider module 14, HSM module 16, and S&R archiving module 18 may all be separably or inseparably connected (e.g. in a PC or a server computer). Also, while in this exemplary embodiment, the archive provider module 14 is discussed as being implemented as a separate entity from the SCP module 15 within a PACS network, it should be understood that it would be possible for the functionality of the archive provider module 14 to be implemented wholly within the SCP module 15.

It should be understood that the exemplary embodiments of the redundant image storage system 10 discussed within this disclosure are for illustrative purpose only and many variations on the specific implementations being discussed are possible. For example, while redundant image storage system 10 is described in relation to two PACS networks, namely source and destination PACS networks, it should be understood that redundant image storage system 10 could encompass any number of PACS networks.

Figure 2:
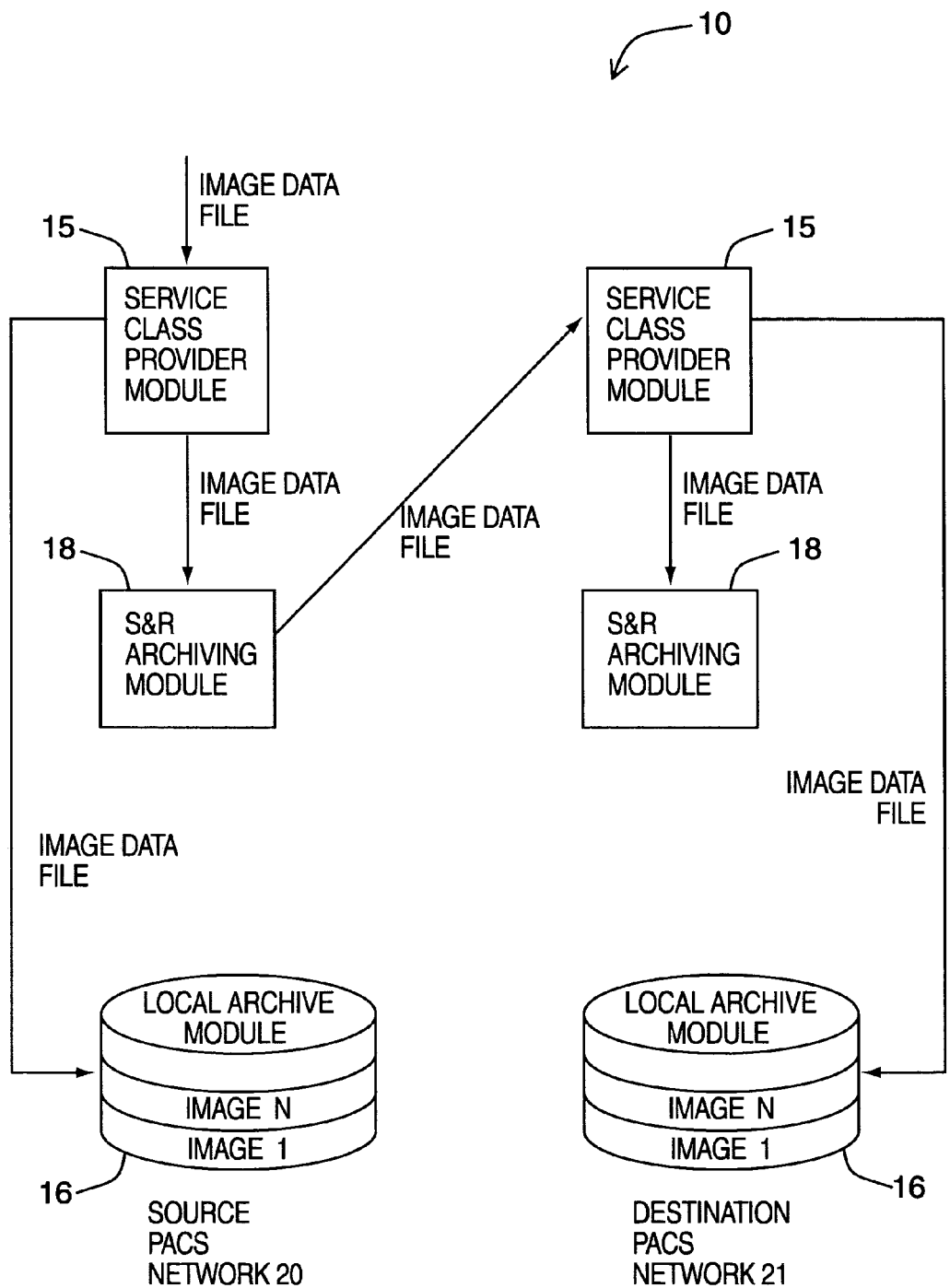
FIG. 2 is an event flow diagram illustrating one exemplary embodiment of the redundant image storage system of FIG. 1.
Figure 3:
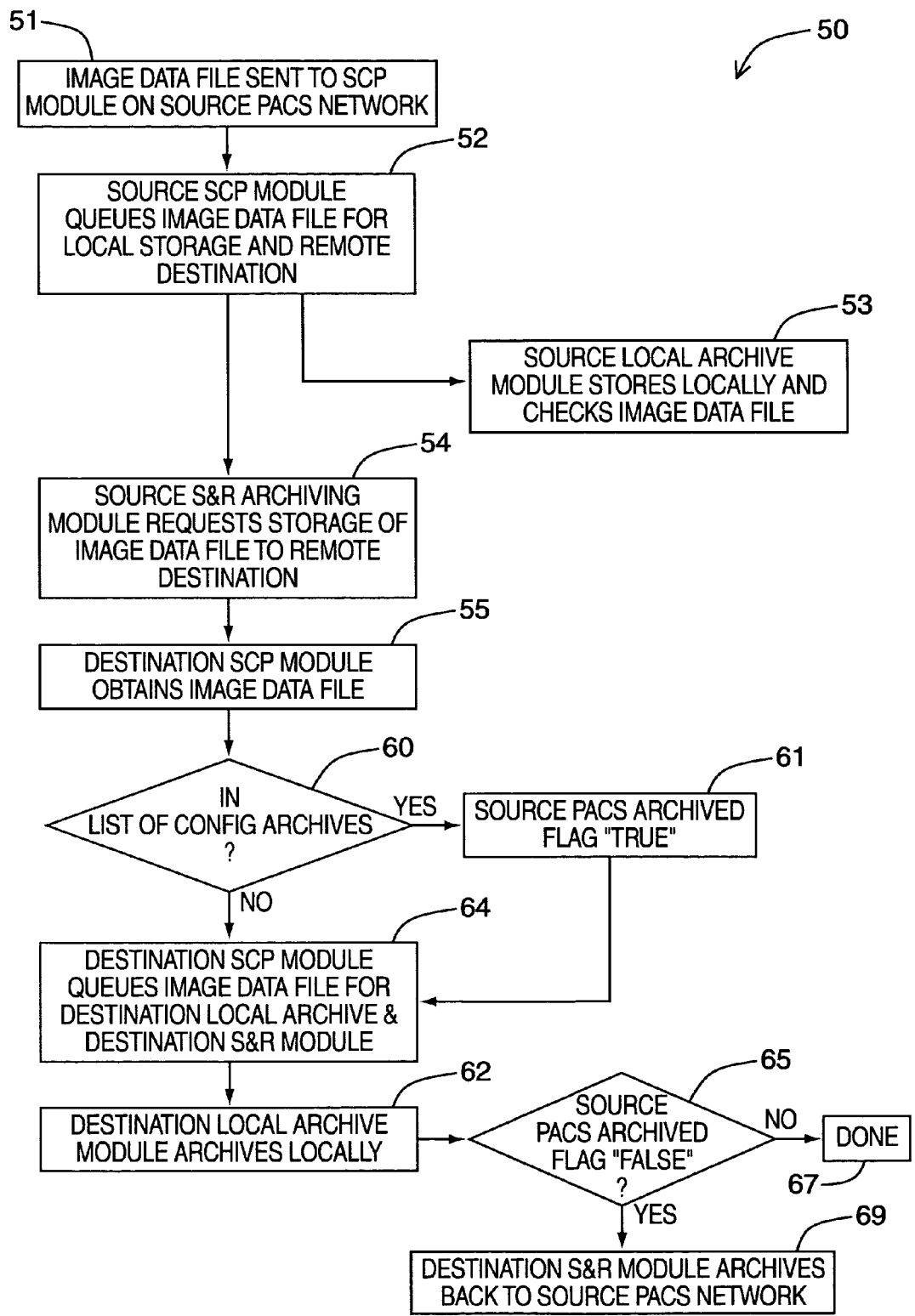
FIG. 3 is a flowchart illustrating the operational steps of the exemplary embodiment of the redundant image storage system of FIG. 2.

Referring now to FIGS. 2 and 3, an exemplary embodiment of the redundant image storage system 10 will be described. Specifically, FIG. 2 is an event flow diagram showing the specific event flow and FIG. 3 is a flowchart illustrating the basic operational steps 50 of redundant image storage system 10 for this exemplary embodiment.

As discussed above, it is assumed that source and destination PACS networks 20 and 21 are configured for archive mirroring as between each other and that source and destination PACS networks 20, 21 can receive image data files directly from image modalities 17, spokes 23 or other PACS networks (i.e. hubs) (not shown).

Operation begins at step (51) where image modality 17 sends image data to acquisition workstation 19 which in turn processes, formats and sends an equivalent image data file to the SCP module 15 of source PACS network 20 (FIG. 2). At step (52), the SCP module 15 of the source PACS network 20 receives the image data file and queues the image data file for archiving within the source HSM module 16 and the S&R archiving module 18 (FIG. 1). At step (53), the image data file is locally archived within the local archive module 16 (in this example the HSM module 16) on the source PACS network 20 (FIG. 2).

As discussed above, the source and destination PACS networks are configured for archive mirroring by configuring S&R archiving modules 18 on the source PACS network 20 to send image data files directly to the SCP module 15 of the destination PACS network 21 (FIG. 2). Accordingly, at step (54), the S&R archiving module 18 of the source PACS network 20 initiates a request for storage of the image data file on the destination PACS network 21 by transmitting a C-STORE request to the SCP module 15 of the destination PACS network 21. The image data file's status and HIS verification status are sent as a part of the C-STORE request to the destination PACS network 21.

At step (55), the SCP module 15 of the destination PACS network 21 receives the C-STORE request, responds and receives the image data file (one object at a time) from the S&R archiving module 18 of the source PACS network 20. If the destination SCP module 15 receives an image data file that already exists in destination PACS network 21, then the image data file is rejected (i.e. the duplicate image data file will not be allowed to overwrite the image data file already in memory within HSM module 16 and the duplicate image data file will not be rerouted to another PACS network). In this case, the SCP module 15 will return a DICOM failure message.

Usually the image data file will not be a duplicate, and so then at step (60), the destination SCP module 15 determines whether the communicating entity (i.e. immediate source which is the source PACS network 20 in this case) is contained within a Remote Archive Locations record (i.e. a listing of configured archives). The Remote Archive Locations record is discussed further below. If so, then at step (61), the destination SCP module 15 registers the image data file as being stored within the S&R archiving module 18 of the destination PACS network 21. That is, a Boolean Source PACS Archived flag that is associated with the image data identifier is set to "true" within the destination S&R module 16. The Boolean Source PACS Archived flag is discussed further below. By doing so, all other coordinating entities of the destination PACS network 21 become aware that the image data file can be obtained, upon request, from the source PACS network 20 by issuing a request to the source S&R archiving module 18.

Regardless of the result of step (60) (i.e. whether the communicating entity is contained or not within the Remote Archive Locations record), at step (64) SCP module 15 of the destination PACS network 21 queues archive requests for the image data file on all configured archives.

At step (62), the image data file is archived locally within the local archive module 16 (in this example the HSM module 16) on the destination PACS network 21.

At step (65), it is determined whether the Source PACS Archived flag is "true" or "false". If the Source PACS Archived flag is "true" then at step (67) specifically does not store back to the source PACS network 20. However, if the Source PACS Archived flag is "false" then at step (69), the destination S&R module 18 archives back to the source PACS network 20.

Thus, in the case where source and destination PACS networks 20 and 21 are configured to archive mirror each other and where source PACS network 20 wishes to store an image data file to destination PACS network 21, the SCP module 15 on destination PACS network 21 receives the image data file from the S&R archiving module 18 on source PACS network 20 and registers it as "PACS archived" on the source PACS network 20 (i.e. by making the Source PACS Archived flag "true"). At this point the destination PACS network 21 will only initiate externally visible requests for the image data file to be archived on other configured archives where the image data file is not already archived (i.e. by referring to the Remote Archive Locations record and the relevant PACS Archived flag).

Figure 4:
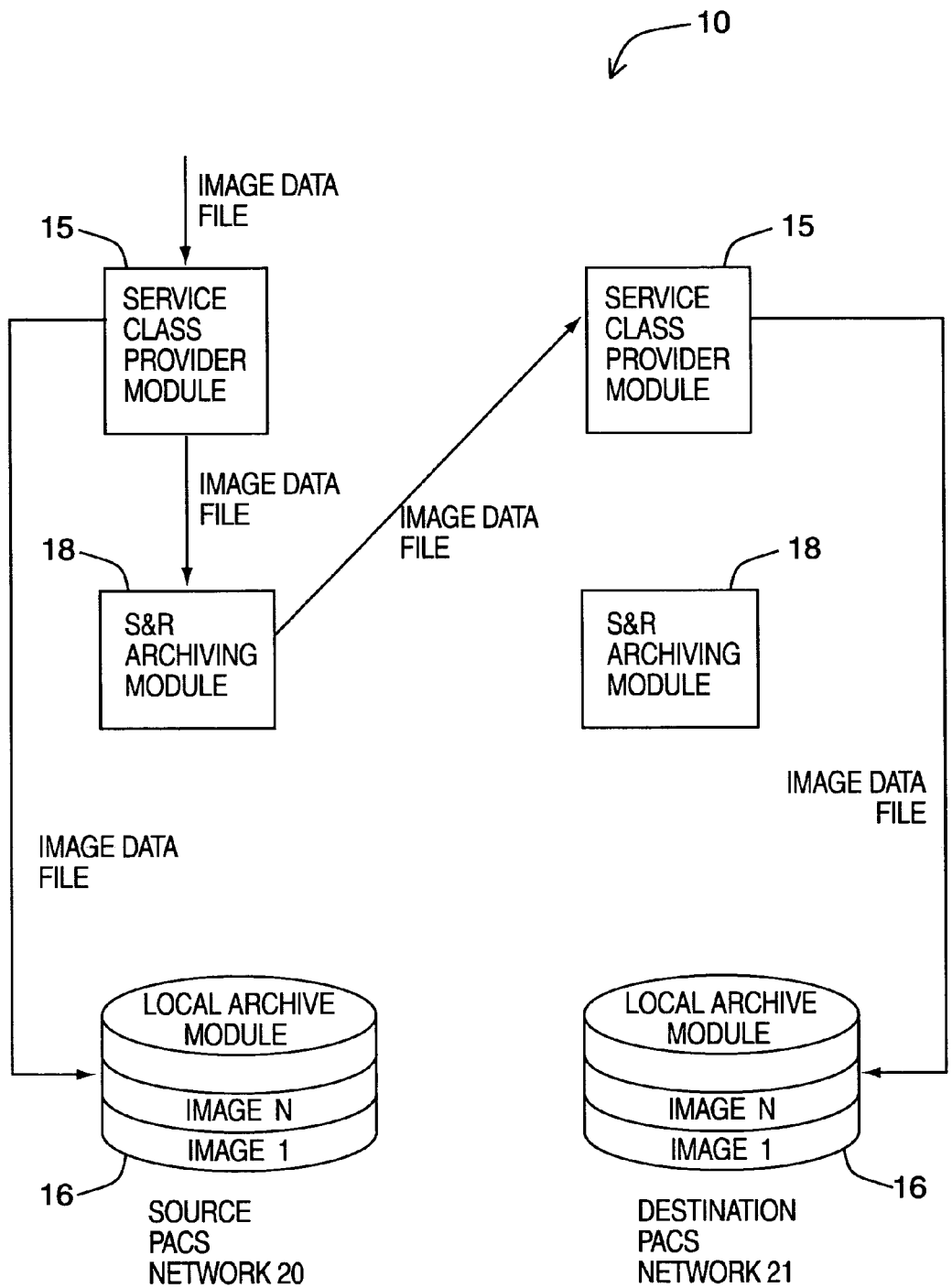
FIG. 4 is an event flow diagram illustrating another exemplary embodiment of the redundant image storage system of FIG. 1.
Figure 5:
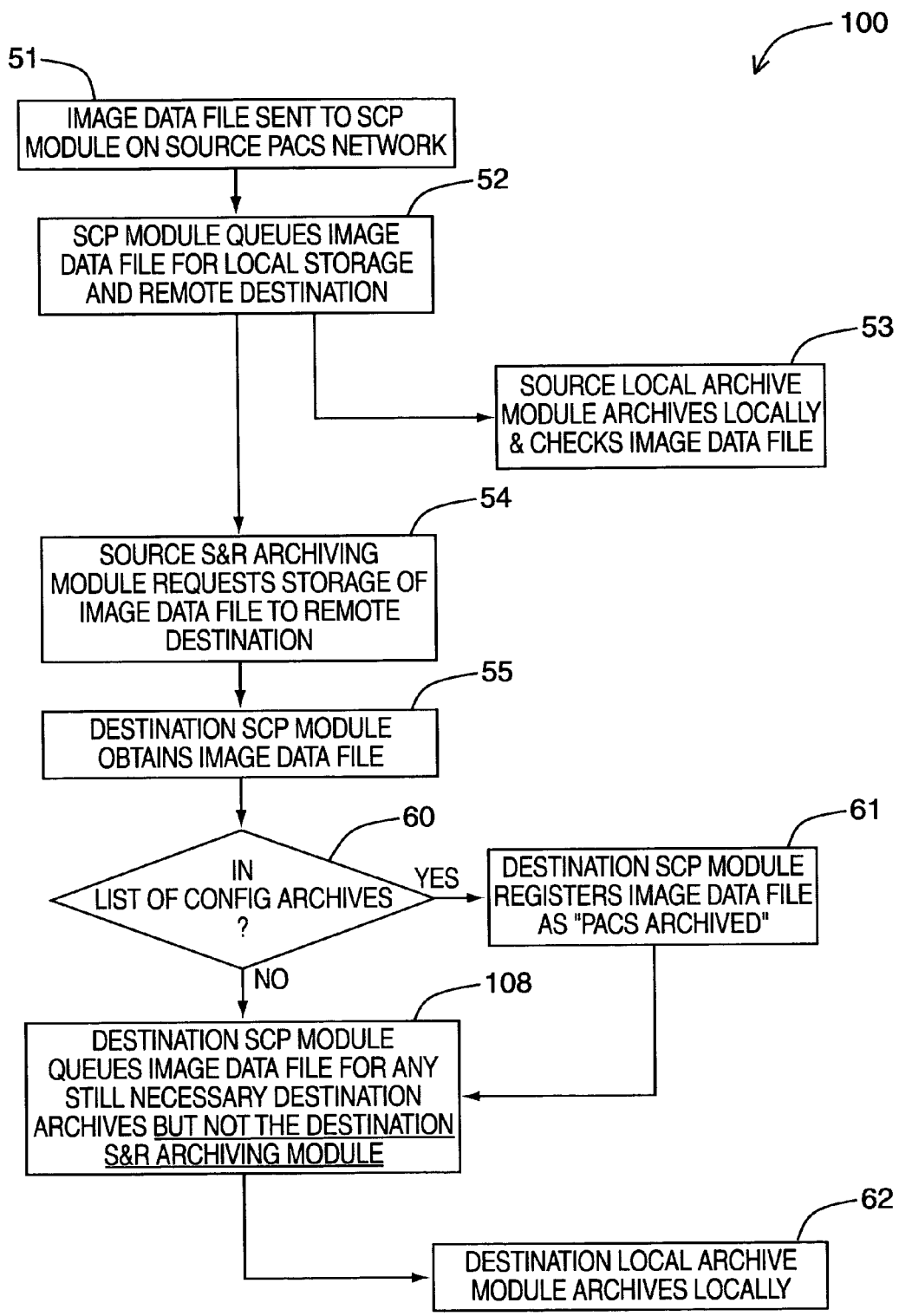
FIG. 5 is a flowchart illustrating the operational steps of the exemplary embodiment of the redundant image storage system of FIG. 4.

Referring now to FIGS. 1, 4 and 5, another exemplary embodiment of the redundant image storage system 10 will be described. Specifically, FIG. 4 is an event flow diagram showing the specific event flow and FIG. 5 is a flowchart illustrating the basic operational steps 100 of redundant image storage system 10 for this exemplary embodiment.

In this exemplary embodiment, extra logic is utilized to exclude the archiving handling when the archiving is done directly as a part of reception rather than as a separate process. That is, as image data files are being received by the SCP module 15 within destination PACS network 21 their source is automatically determined and if it is determined to be one of the S&R archive destinations, it registers it as "PACS Archived" from the source at step (61). As standard safeguards of archiving processes include prevention of registered redundant storage, this is a sufficient change to prevent redundant storage "looping" discussed above.

This embodiment is otherwise identical to the first embodiment described in relation to FIGS. 2 and 3. The present exemplary embodiment shares the same steps and descriptions except for step (64) of FIG. 3. In lieu of step (64) that follows after steps (60) and (61) we proceed instead to step (108). At step (108), internal jobs are only queued for those archives that are not already flagged as complete. This results in extra internal savings of effort, while maintaining the same degree of external efficiency.

Figure 6:
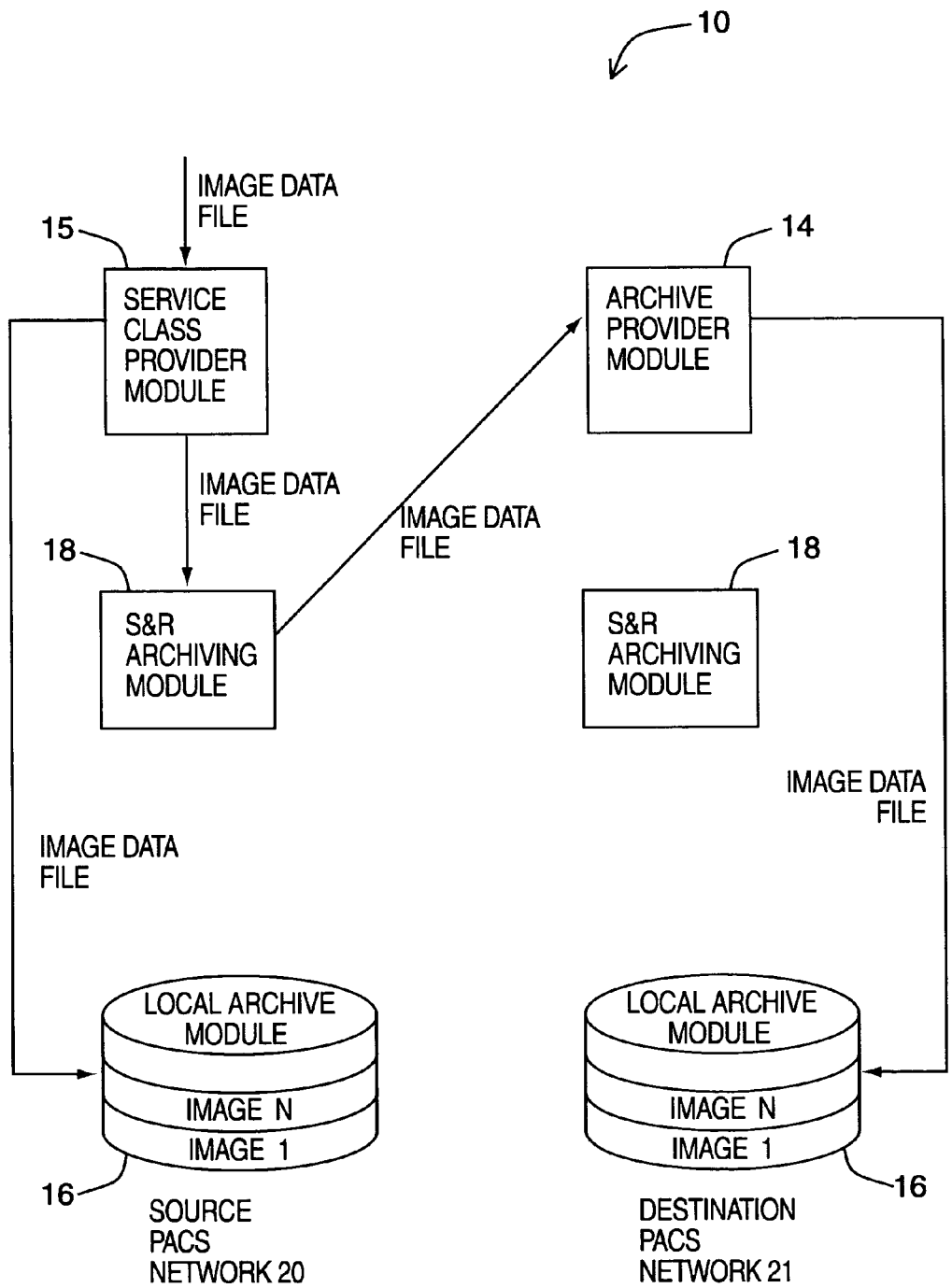
FIG. 6 is an event flow diagram illustrating another exemplary embodiment of the redundant image storage system of FIG. 1.
Figure 7:
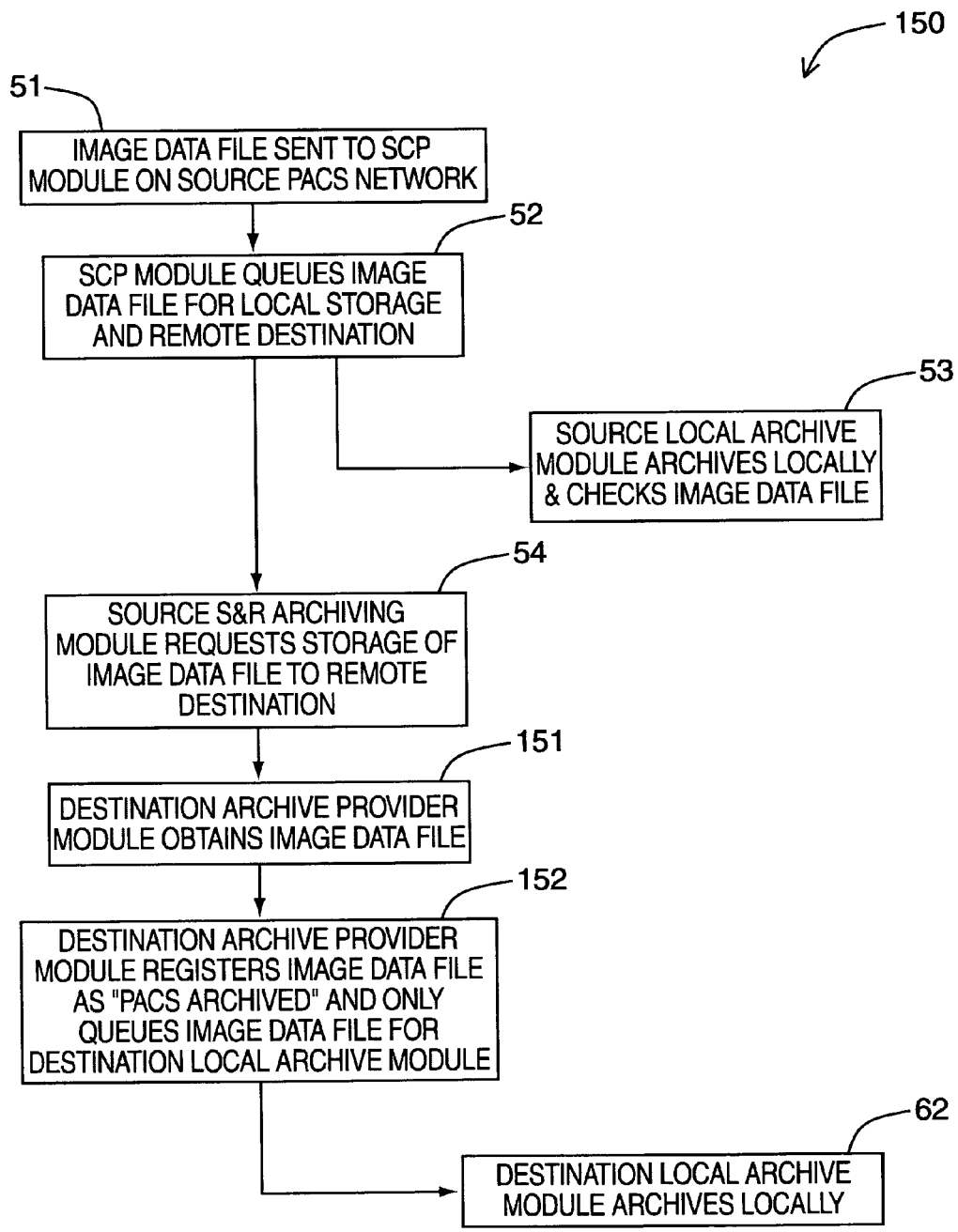
FIG. 7 is a flowchart illustrating the operational steps of the exemplary embodiment of the redundant image storage system of FIG. 6.

Referring now to FIGS. 1, 6 and 7, another exemplary embodiment of the redundant image storage system 10 will be described. Specifically, FIG. 6 is an event flow diagram showing the specific event flow and FIG. 7 is a flowchart illustrating the basic operational steps 150 of redundant image storage system 10 for this exemplary embodiment.

In this exemplary embodiment, the handling of incoming image data files for archiving is handled through a separate communication channel. This communication channel would typically (but not necessarily) be related to the normal image data file flow but would only be used by the archive systems. Accordingly, the detection of whether the source of the transmission of the image data file is an archive location would be handled implicitly via the usage of the separate channel, rather than through the use of a comparison.

The archive provider module 14 within the destination PACS network 21 is utilized to receive the image data file at (151) from the S&R archiving module 18 associated with the source PACS network 20. Upon receipt of the image data file, the destination archive provider module 14 submits (i.e. queues) the image data file for local archiving within the HSM module 16 of the destination PACS network 21 at (152).

In this way, the destination archive provider module 14 ensures that a request is not sent to source PACS network 20 since it is assumed that the image data file is already archived on the source PACS network 20. That is, destination archive provider module 14 enables the image data file to be archived locally but not where it has already been archived.

However, it should be understood that since the SCP module 15 associated with the source PACS network 20 has already conducted various operations on the image data file, the archive provider module 14 unlike the SCP module 15, does not generally need to perform field mappings or OCR, HIS verify (unless the image data file failed HIS verification or was not verified on the source of transmission), or compress the image data file (unless not already compressed).

As discussed above, in the case where archive mirroring is desired, the S&R archiving modules 18 on each PACS network can be configured to send image data files directly to the archive provider module 14 instead of the SCP module 15.

In this exemplary embodiment, the archive provider module 14 is implemented as a separate component from the SCP module 15 within network gateway 12. This configuration allows for efficient implementation of the effective archiving mirroring procedure discussed above. Since archive provider module 14 is separate from the SCP module 15 (i.e. not included within the SCP module 15), it is not necessary for SCP users to be re-trained on the behaviour and configurations of the SCP module 15. It is contemplated that if the archive provider module 14 was not separate from the SCP module 15, the documentation, installation and serviceability of the SCP module 15 would be substantially more difficult.

Referring now to FIGS. 3 and 7, the first four steps (51-54) in FIG. 7 are the same as the first exemplary embodiment as illustrated in FIG. 3. The next step, as shown in FIG. 7 is step (151). At step (151), the destination archive provider module 14 of the destination PACS network 21 receives the image data file and registers the image the same way that the SCP module 15 did in previous exemplary embodiments. At step (152), the destination archive provider module 14 sets the Boolean "PACS Archived flag" for all PACS archives for the received image data identifier to "true". It can do this based on the implicit supply of information that the image is to be stored across the entire hub.

Finally, at step (62), the archive provider module 14 submits storage requests to all non-PACS archives (i.e. all local archives). Notice that in this embodiment, even more efficiency is gained, at the small cost of increased set-up and maintenance.

Figure 8:
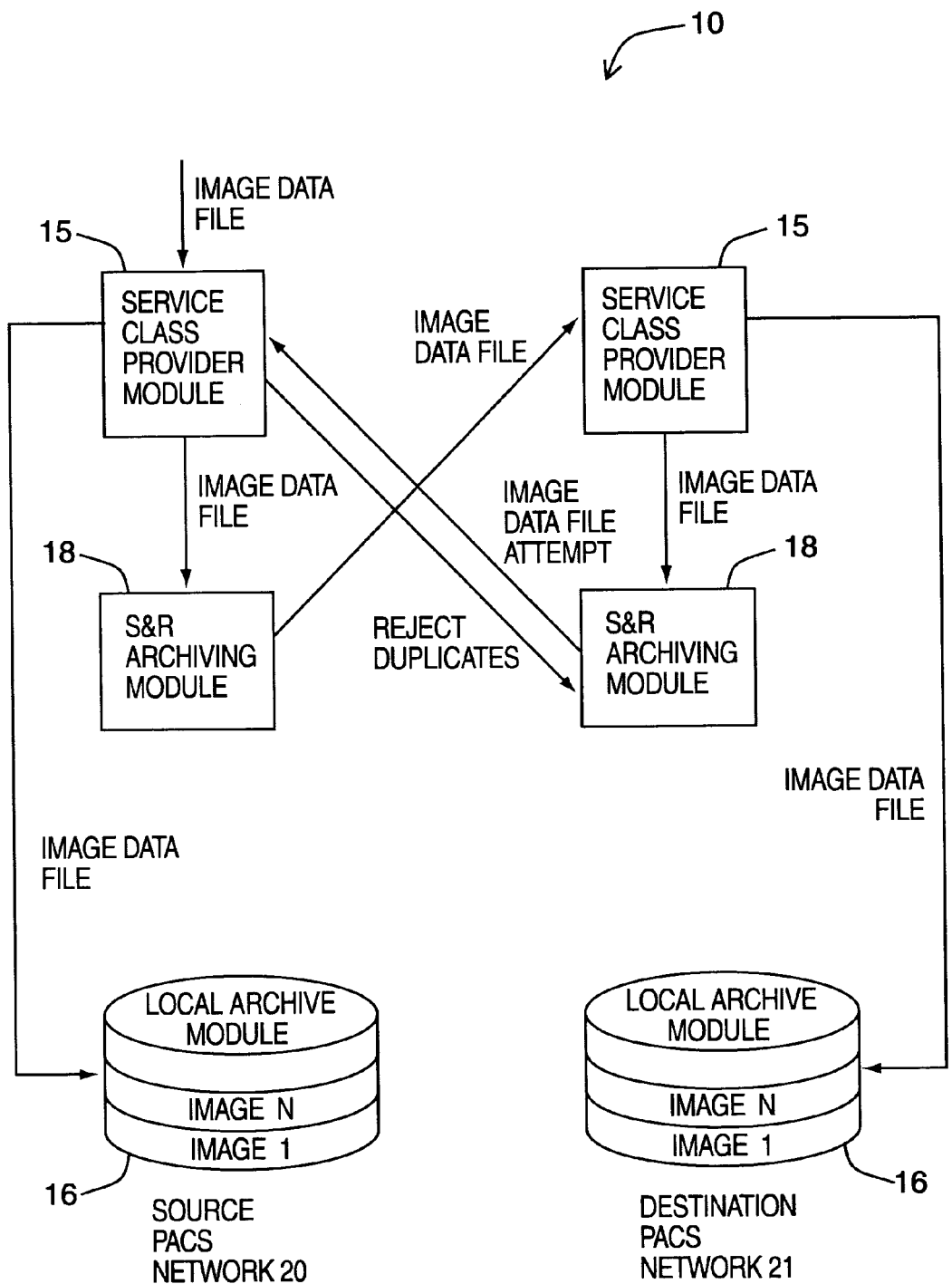
FIG. 8 is an event flow diagram illustrating another exemplary embodiment of the redundant image storage system of FIG. 1.
Figure 9:
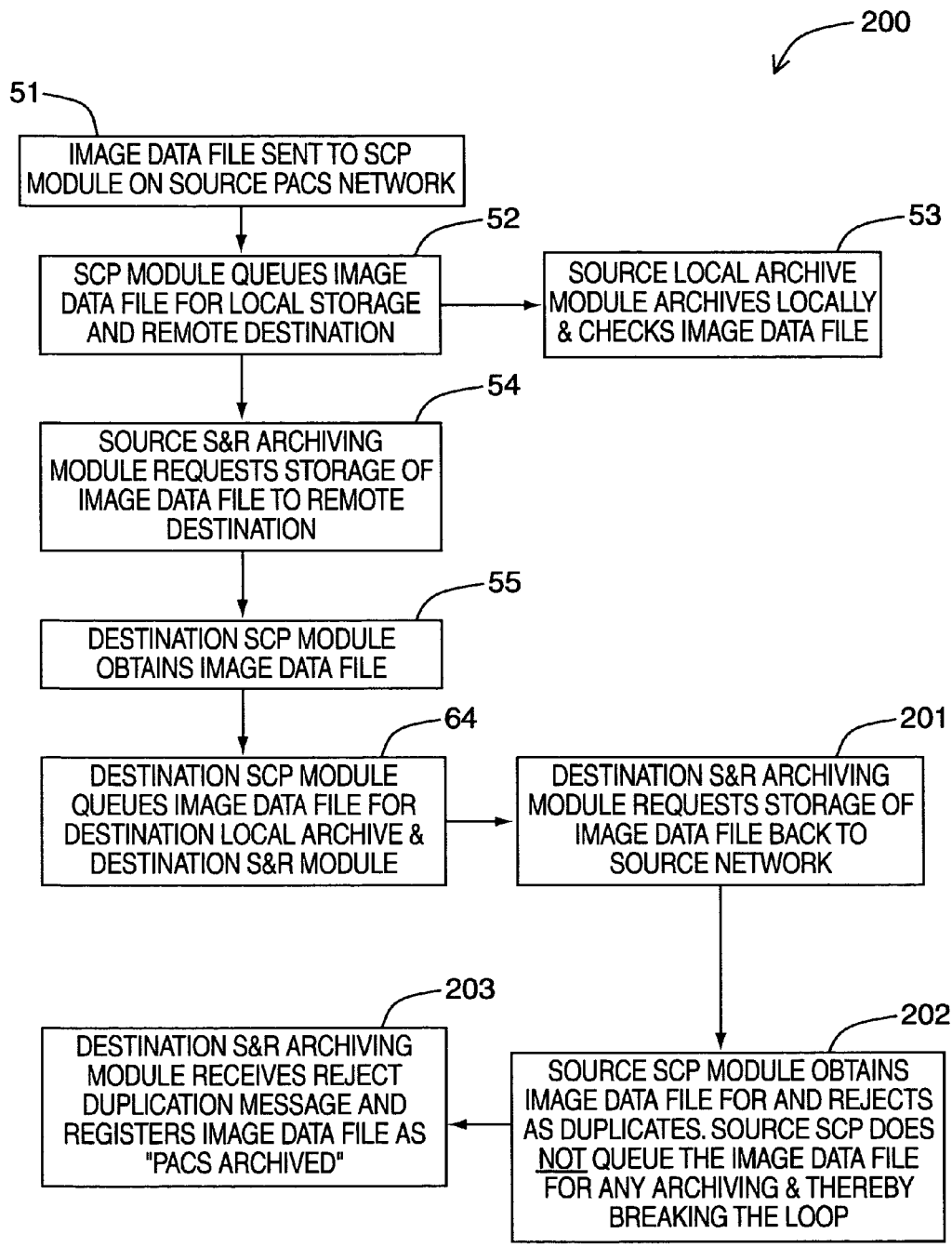
FIG. 9 is a flowchart illustrating the operational steps of the exemplary embodiment of the redundant image storage system of FIG. 8.

Referring now to FIGS. 1, 8 and 9, another exemplary embodiment of the redundant image storage system 10 will be described. Specifically, FIG. 8 is an event flow diagram showing the specific event flow and FIG. 9 is a flowchart illustrating the basic operational steps 200 of redundant image storage system 10 for this exemplary embodiment.

In this exemplary embodiment, the destination PACS network 21 is used to directly indicate that an archived copy of the image data file is available on the source PACS network 20. This could be either the destination PACS network 20 or another PACS network transmitting the image data file within the redundant image storage system 10. Also, since conventional SCP modules 15 within PACS networks reject duplicates this feature could be utilized to determine whether destination PACS network 21 should send additional archiving requests.

Steps (51) to (55) are the same as the first embodiment as shown in FIG. 3. The image data file is transmitted to the source PACS network 20, and from there to the destination PACS network 21 through the destination SCP module 15. At step (64) the destination SCP 15 queues requests to store the image data file on both the local and PACS archives.

At step (201) the S&R module 18 of the destination PACS queries (C-FIND) or blindly attempts to transmit (C-STORE) the image data file back to the SCP module 15 of the source PACS network. At this point the loop would be complete but for the safety mechanism of the SCP module 15 that rejects duplicates. Step (202) specifies this decision of the source of transmission, wherein it returns a specific known failure code, and does not process further.

At step (203) the S&R module 18 of the destination PACS network recognizes the error code and registers the image data identifier as being archived successfully, but emptily, on the source PACS network 20.

It should be noted that this embodiment, while meeting the rudimentary goals does so with little elegance or efficiency. Practically it is also only applicable where the behavior of both source and destination are under full control.

Figure 10:
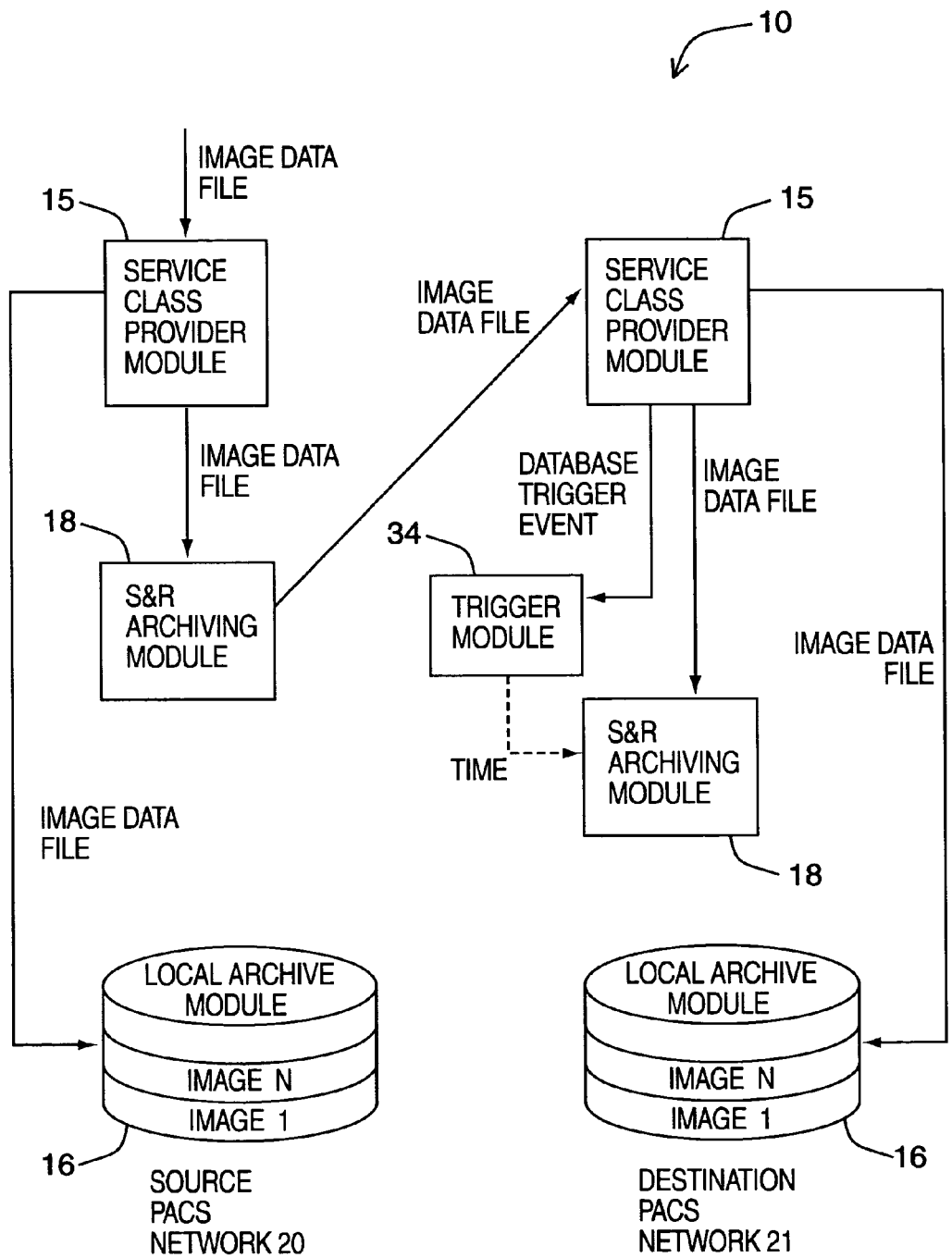
FIG. 10 is an event flow diagram illustrating another exemplary embodiment of the redundant image storage system of FIG. 1.
Figure 11:
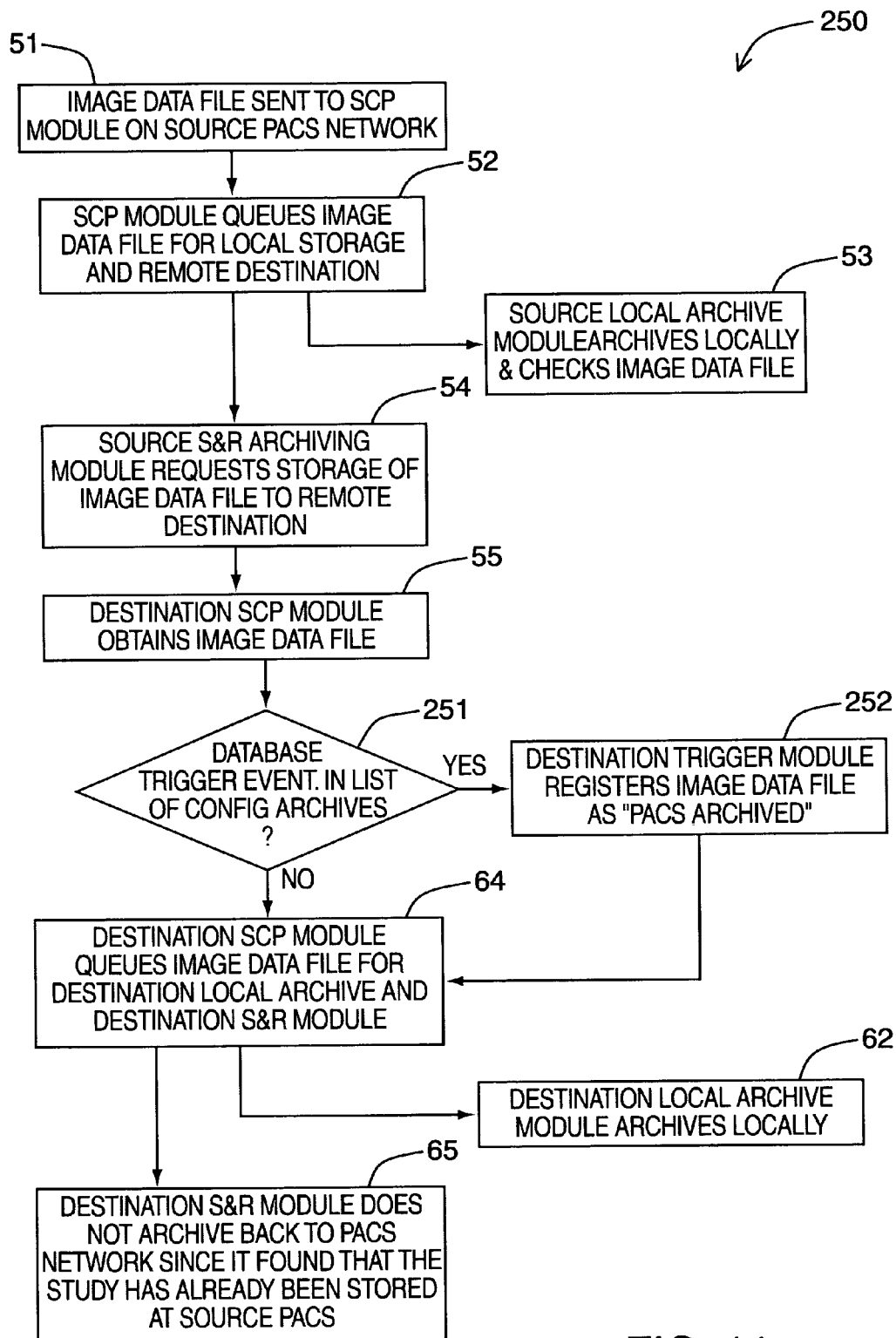
FIG. 11 is a flowchart illustrating the operational steps of the exemplary embodiment of the redundant image storage system of FIG. 10.

Referring now to FIGS. 1, 10 and 11, another exemplary embodiment of the redundant image storage system 10 will be described. Specifically, FIG. 10 is an event flow diagram showing the specific event flow and FIG. 11 is a flowchart illustrating the basic operational steps 250 of redundant image storage system 10 for this exemplary embodiment.

In this exemplary embodiment, the extra logic utilized to exclude the archiving handling is embodied in a separate component called a trigger module 34. The trigger module 34 operates by observing the effects of the destination SCP module 15 that receives images in the database. The trigger module 34 monitors the status of database events within the network gateway 12. Database events such as "new study added" or "HIS verification request" could each be considered a triggering event and would cause the trigger module 34 to determine the source of the recently transmitted image data. If the source is one of the "Store and Remember" destinations it would actively register the image as already archived there. Again, any of the strategies for reducing the other unnecessary work could also be employed, but are not needed for the present exemplary purposes.

By excluding changes and checks from the direct flow of control, there are certain race conditions present in this embodiment, which are actually practical in the commercial application in the usual case.

Referring now to FIGS. 1, 10, and 11, at step (55) the SCP module 15 of the destination PACS network 21 updates the common database with new events and records. These events cause an independent component to begin processing at step (251). That is in this step, the trigger module 34 evaluates whether these new events and records represent image data files present on the source PACS network that is also known as a "Store and Remember" destination.

If so, then at step (252) the destination trigger module 34 proceeds to set the Boolean Source PACS Archived flag to "true". This is completed in a more timely fashion than the workflow arriving at the archiving of the image data file in the S&R archive module 18. As discussed above, the database triggering event mechanism as administered by the trigger module 34 acts as an independent process or agent. Also, it should be understood that the various control flows are coordinated at the high level by the SCP module 15 which in turn handles queuing based on the state saved by the trigger module 34. Therefore, at step (65) the destination S&R archive module 18 determines that the storage request is not necessary since the Source PACS Archive flag has been set to true.

While the various exemplary embodiments of the image display system 10 have been described in the context of medical image management in order to provide an application-specific illustration, it should be understood that image display system 10 could also be adapted to any other type of image or document display system.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

While certain features of the invention has been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A redundant medical image storage system for archiving a medical image data file having an image data identifier within at least two mirrored picture archiving and communication system (PACS) networks, said system comprising:
   (a) a mirrored source PACS network including:
      (i) a source storage device for storing the medical image data file;
      (ii) a source processor coupled to the source storage: device, the source processor being adapted to:
         (A) receive the medical image data file and store the medical image data file in the source storage device;
         (B) transmit the medical image data file received by the source processor to at least one other mirrored PACS network;
   (b) a first mirrored destination PACS network coupled to the mirrored source PACS network, the first mirrored destination PACS network including:
      (i) a Boolean source PACS Archived flag associated with the image data identifier and the mirrored source PACS network;
      (ii) a destination storage device for storing the medical image data file;
      (iii) a destination processor coupled to the destination storage device, said destination processor being adapted to:
         (A) receive the medical image data file from the mirrored source PACS network and store the medical image data file in the destination storage device;
         (B) determine whether the medical image data file should also be stored back in the mirrored source PACS network;

(C) if (B) is false, then setting the value of the source PACS Archived flag to true;

(D) transmit the medical image data file received from the mirrored PACS source network to the mirrored source FACS network for storage only if the source PACS Archived flag is false.

2. The redundant medical image storage system of claim 1, wherein the destination storage device and the destination processor are further adapted to store and maintain a Remote Archive Locations record comprising a list of configured PACS archive networks and where the determination in (B) is made by determining whether the mirrored source PACS network is contained within the Remote Archive Locations record.

3. The redundant medical image storage system of claim 2, further comprising a second mirrored destination PACS network contained within the Remote Archive Locations record, and where the destination storage device and destination processor of the first mirrored destination PACS network are further adapted to maintain a Boolean second destination PACS archived flag associated with the image data identifier and the first mirrored destination PACS network, and where the first mirrored destination PACS network transmits the medical image data file received from the mirrored source PACS network to the second mirrored destination PACS network if the second destination PACS Archived flag is false.

4. The redundant medical image storage system of claim 2, wherein the destination processor is further adapted to determine whether a database triggering event associated with a medical image data file has occurred within the destination storage device and if so, making the determination in (B) by determining where the medical image data file originated.

5. The redundant medical image storage system of claim 4, wherein the database triggering event is selected from a group consisting of: a new study added event and a HIS (Hospital Information System) verification check event.

6. The redundant medical image storage system of claim 1, wherein the destination storage device is adapted to receive the medical image data file from a separate communication channel and where the determination in (B) is made by determining whether the medical image data file was received over the separate communication channel.

7. The redundant medical image storage system of claim 1, wherein the source storage device is adapted to reject any duplicate medical image data files, and where the determination in (B) is made by determining whether a duplicate medical image data file has been transmitted.

8. A method for archiving a medical image data file having an image data identifier within at least a mirrored source archiving and communication system (PACS) network and a first mirrored destination archiving and communication system (PACS) network, wherein the first mirrored destination PACS network includes a destination storage device said method comprising:
(a) receiving the medical image data file;
(b) storing the medical image data file in a source storage device of the mirrored source PACS network;
(c) retrieving the medical image data file from the source storage device of the mirrored source PACS network;
(d) transmitting the medical image data file received in (a) to the first mirrored destination PACS network;
(e) associating a Boolean source PACS Archived flag with the medical image data identifier and the mirrored source PACS network;

(f) receiving the medical image data file from the mirrored source PACS network and storing the medical image data file in the destination storage device of the first mirrored destination PACS network;
(g) determining whether the medical image data file should also be stored back in the mirrored source PACS network;
(h) if (g) is false, then setting the value of the source PACS Archived flag to true; and
(i) transmitting the medical image data file received from the mirrored source PACS network to the mirrored source PACS network for if the source PACS Archived flag is false.

9. The method of claim 8, further comprising storing and maintaining a Remote Archive Locations record comprising a list of configured PACS archive networks at the first mirrored destination PACS network and where the determination in (g) is made by determining whether the mirrored source PACS network is contained within the Remote Archive Locations record.

10. The method of claim 9, wherein the Remote Archive Locations record contains a second mirrored destination PACS network and further comprising maintaining a Boolean second destination PACS archived flag associated with the image data identifier and the second mirrored destination PACS network and sending the medical image data file received from the mirrored source PACS network from the first mirrored destination PACS network to the second mirrored destination PACS network if the second destination PACS archived flag is false.

11. The method of claim 9, further comprising determining whether a database triggering event associated with an medical image data file has occurred within the destination storage device of the first mirrored destination PACS network and if so, making the determination in (g) by determining where the medical image data file originated.

12. The method of claim 11, wherein the database triggering event is selected from a group consisting of a new study added event and a HIS (Hospital Information System) verification check event.

13. The method of claim 8, wherein the destination storage device is adapted to receive the medical image data file from a separate communication channel and where the determination in (g) is made by determining whether the medical image data file was received over the separate communication channel.

14. The method of claim 8, wherein the source storage device is adapted to reject a duplicate medical image data file, and where the determination in (g) is made by determining whether a duplicate medical image data file has been transmitted.

15. A non-transitory computer-readable storage medium upon which a plurality of instructions are stored, the instructions for performing the steps of the method as claimed in claim 8.

16. The redundant medical image storage system of claim 1, wherein the destination processor is further adapted to obtain the medical image data file from the mirrored source PACS server if the source PACS Archived flag is true.

17. The redundant medical image storage system of claim 2, wherein the destination processor is further adapted to obtain the medical image data file from the mirrored source PACS server if the mirrored source PACS server is listed in the Remote Archive Locations record and the source PACS archive flag is true.

18. The method of claim 8, further comprising obtaining the medical image data file from the mirrored source PACS server if the source PACS Archived flag is true.

19. The method of claim 9, further comprising obtaining the medical image data file from the mirrored source PACS server if the mirrored source PACS server is listed in the Remote Archive Locations record and the source PACS archive flag is true.

* * * * *